United States Patent [19]

Petritsch et al.

[11] 4,028,407

[45] June 7, 1977

[54] METHOD OF PRODUCING TARTARIC ACID

[75] Inventors: Klaus Petritsch, Weissenstein (Drau); Peter Korl, Feistritz, both of Austria

[73] Assignee: Firma/Osterreichische Chemische Werke Gesellschaft m.b.H, Mariahilfer Gurtel, Austria

[22] Filed: Dec. 18, 1975

[21] Appl. No.: 641,875

[30] Foreign Application Priority Data

Dec. 20, 1974 Austria .............................. 10215/74

[52] U.S. Cl. ................................................ 260/536
[51] Int. Cl.² ........................................ C07C 59/14
[58] Field of Search ................................... 260/536

[56] References Cited

UNITED STATES PATENTS 3,769,339  10/1973  Wagner et al. ..................... 260/536

OTHER PUBLICATIONS

Church, J. M. et al., Ind. Engineering Chem. 43, p. 1780 (1951).

*Primary Examiner*—Paul J. Killos

*Attorney, Agent, or Firm*—Watson, Cole, Grindle & Watson

[57] ABSTRACT

Tartaric acid is produced by epoxidizing acid calcium maleate with aqueous hydrogen peroxide in the presence of a tungstic acid-containing catalyst to produce sparingly soluble acid calcium cis-epoxysuccinic acid, which is suspended in a solvent medium comprising an organic solvent or a mixture of organic solvent and water and treated with sulphuric acid. Calcium sulphate is formed and separated and the liberated organic acids consisting essentially of epoxysuccinic acid are then hydrolyzed in an aqueous medium to form tartaric acid. The organic solvent may be one in which epoxysuccinic acid is soluble and may be immiscible or miscible with water. If the solvent is imiscible with water the epoxysuccinic acid may be transferred to the aqueous medium in which it is hydrolyzed by liquid-liquid extraction. The epoxysuccinic acid may be crystallized out of the solvent medium and thereafter dissolved in water for the hydrolysis, or, if the organic solvent is miscible with water and the solvent medium comprises water, the organic solvent may be distilled off to leave the epoxysuccinic acid in the aqueous medium in which hydrolysis can be effected. Various organic solvents are disclosed as suitable.

12 Claims, No Drawings

METHOD OF PRODUCING TARTARIC ACID

FIELD OF THE INVENTION

This invention relates to a method of producing tartaric acid.

PRIOR ART

J. M. Church and R. Blumberg (Ind. Engng. Chem. 43 (1951), 1780) have described a method of producing tartaric acid from maleic acid and hydrogen peroxide. The maleic acid is epoxidised with hydrogen peroxide in the presence of tungstic acid and the cis-epoxysuccinic acid formed is hydrolysed into tartaric acid which is crystallised by cooling the reaction solution and filtered off, the mother liquor being recycled to the epoxidation stage. The reaction takes place in accordance with the following reaction scheme:

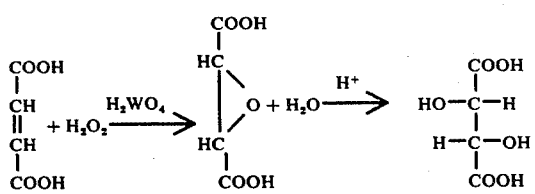

A disadvantage of this method is that the mother liquor still contains maleic acid, the catalyst, and an amount of tartaric acid corresponding to the solubility product. When this mother liquor is used, the addition of hydrogen peroxide gives rise to a number of side reactions entailing the formation of permaleic acid, maleic acid, fumaric acid, acetaldehyde, pyruvic acid, and formic acid. Another disadvantage of this method is that the tartaric acid forms with the catalyst a stable tungsten complex, so that the tungstic acid is inactivated as an epoxidation catalyst. This complex also makes the quantitive recovery of the catalyst practically impossible without having to destroy all the organic substances present.

In French Patent Specification No. 2,040,732 a cyclic process for the production of tartaric acid is described, in which it is attempted to avoid the difficulties mentioned above. An aqueous solution of maleic acid is epoxidised into epoxysuccinic acid with the aid of hydrogen peroxide, the epoxysuccinic acid is hydrolysed into tartaric acid, the tartaric acid is crystallised by cooling the reaction solution and filtered off and the remaining tartaric acid is precipitated from the mother liquor in the form of an alkali or alkaline earth metal salt.

This method has the disadvantage that the epoxidation of free maleic acid does not take place quantitatively. Tartaric acid is formed even during the epoxidation and thus there are losses of yield because of the side reactions mentioned in connection with the first method described above. In addition to these losses of yield, the formation of a not inconsiderable amount of difficulty utilisable calcium tartrate is observed.

As is clear from German Published Specification No. 2,400,767, an epoxysuccinic acid of any origin may be used as a starting product for hydrolysis into tartaric acid, whereupon according to that specification the hydrolysis is effected in the presence of certain metal compounds as catalysts. The methods of producing epoxysuccinic acid which are mentioned include the epoxidation of acid calcium maleate into acid calcium epoxysuccinate in the presence of a tungsten compound as catalyst, followed by decomposition with acid. During this acid decomposition of the calcium epoxysuccinate, which is effected in an aqueous medium, and the hydrolysis of the free epoxysuccinic acid formed in the aqueous solution, it is, however, impossible to prevent the introduction of calcium salts into the final product and, because of the metal compounds used as catalysts for the hydrolysis, it is impossible to prevent the risk of biologically problematical heavy metal ions from passing into the tartaric acid obtained as the final product, which is objectionable from the hygienic point of view for a substance of this kind, which is particularly important for the foodstuffs industry.

In order to achieve a technically improved process it would be essential to use a particularly pure epoxysuccinic acid free from prematurely formed tartaric acid (which may give rise to undesirable or disturbing side reactions), and to be able to subject this substance to hydrolysis which would proceed smoothly and give high yields.

SUMMARY OF THE INVENTION

It has now been found that a tartaric acid free from admixtures which are undesirable or are objectionable from the health point of view can be obtained, starting with an acid calcium epoxysuccinate formed by the epoxidation of acid calcium maleate, by a simple method which takes place smoothly, if the decomposition of the acid calcium epoxysuccinate does not take place in an aqueous suspension, but in an organic or organic-aqueous reaction medium, whereupon the resulting mixture of organic acids essentially containing epoxysuccinic acid is subjected to hydrolysis after transfer to an aqueous medium.

Accordingly the present invention provides a method of producing tartaric acid, comprising the steps of epoxidising acid calcium maleate with hydrogen peroxide in the presence of a tungstic acid-containing catalyst, separating from the reaction medium the resulting sparingly soluble acid calcium epoxysuccinate, suspending the acid calcium epoxysuccinate in a solvent medium which is an organic solvent or a mixture of water and an organic solvent, reacting the acid calcium epoxysuccinate suspended in the solvent medium with sulphuric acid, separating from the solvent medium the calcium sulphate formed as the result of the addition of sulphuric acid, recovering from the solvent medium the liberated organic acids consisting essentially of epoxysuccinic acid in a substantially pure state and substantially free from calcium salt, and effecting hydrolysis of said epoxysccinic acid to tartaric acid in an aqueous medium.

DETAILED DESCRIPTION OF THE INVENTION

The present method is therefore based essentially on the fact that the acid calcium salt of cis-epoxysuccinic acid which is obtained by the epoxidation, and which because of its low solubility product in water is precipitated from the reaction solution and thus is not subjected to further oxidation, is first suspended in an organic or organic-aqueous solvent and reacted with sulphuric acid to form calcium sulphate and free organic acid, which is essentially epoxysuccinic acid. The calcium sulphate precipitated is separated, for example in a filtration stage and, depending upon the nature of the organic solvent, the filtrate is further treated to recover the freed organic acids. The freed organic acids can preferably be recovered by liquid-liquid extraction in the case of solvents immiscible with water, and, in the case of solvents which are miscible with water, by evaporation of the organic solvent, followed by crystallisation of the remaining aqueous solution, or by direct utilisation of this aqueous residue. In any case the resulting epoxysuccinic acid is finally converted into tartaric acid by hydrolysis in conventional manner. The mixture of free organic acids which is formed in the organic medium by liberation with sulphuric acid, and which consists essentially of epoxysuccinic acid, surprisingly supplies as end product on hydrolysis, with a high yield and without incurring losses through disturbing side reactions, a tartaric acid of very high purity, which is also free from calcium salts and undesirable heavy metal compounds. The present method in fact provides the advantage that during the precipitation of calcium sulphate, despite the presence of sulphuric acid, practically no tartaric acid formed by premature hydrolysis can be simultaneously precipitated as calcium salt.

The expoxidation reaction can be carried out at a temperature of from 50° to 90° C. and the end of the reaction can be recognised by the complete consumption of the hydrogen peroxide. Tungstic acid anhydride $WO_3$, tungstic acid, a salt of tungstic acid, silicotungstic acid or phosphortungstic acid may be used as the catalyst, the catalyst being used in an amount of from 0.1 to 1% by weight, calculated as $WO_3$, in aqueous solution. The concentration of the acid calcium maleate is not critical. The starting solution may be a dilute, saturated, or even a supersaturated solution. When working, for example, with an excess of calcium maleate, only a part of the same is at first in solution, while the remainder is suspended in undissolved form. During the epoxidation the whole amount then gradually dissolves. A limit is however imposed by the fact that the suspension must at all times be able to be thoroughly stirred. The hydrogen peroxide should be added in such a manner that the internal temperature does not rise by more than 5° to 10° C. It can be used in all usual commercial concentrations of from 30 to 70% by weight.

It is expedient to work with a dilute calcium maleate solution (about 10 to 30% strength) during the epoxidation and to add the acid calcium maleate and hydrogen peroxide in equimolar amounts at determined intervals of time, until the quantitative capacity of the reactor has been reached. The acid calcium epoxysuccinate is then filtered off and the mother liquor is recycled for another epoxidation operation.

In the reaction of the present method, epoxysuccinic acid must be liberated and finally hydrolysed to tartaric acid by heating in aqueous solution. The liberation of an organic acid from its calcium salt is usually effected with sulphuric acid in an aqueous solution, and in the case of acid calcium tartrate takes place in accordance with the following:

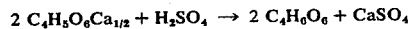

$$2\ C_4H_5O_6Ca_{1/2} + H_2SO_4 \rightarrow 2\ C_4H_6O_6 + CaSO_4$$

This conventional process, however, cannot be employed in the case of the recovery of cis-epoxysuccinic acid, because during the reaction with sulphuric acid in aqueous solution at the temperature required for this purpose, the hydrolysis of the freed epoxysuccinic acid to tartaric acid is already started because of the high hydrogen ion concentration. Unlike natural L (+)-tartaric acid, the DL tartaric acid produced in this manner will in fact form a sparingly soluble calcium salt, so that calcium tartrate will be present in the resulting calcium sulphate and there will be losses of yield.

Since an essential feature of the invention is now due to the fact that the conversion of the acid calcium salt of epoxysuccinic acid with sulphuric acid to form free epoxy acid and calcium sulphate is effected with the aid of a reaction medium comprising an organic or organic-aqueous solvent, a solvent suitable for this purpose must fulfil various requirements: epoxysuccinic acid must be adequately soluble in the respective solvent, while the solvent must not react with epoxysuccinic acid and in addition it must be sufficiently stable to concentrated sulphuric acid and water under process conditions.

There are two main possibilities for the solvent for the conversion of acid calcium epoxysuccinate to free epoxysuccinic acid and calcium sulphate with the aid of sulphuric acid:

a. The organic solvent is immiscible with water or is miscible with water only to so slight an extent that the formation of separate liquid phases is possible.

These solvents are principally various esters, preferably esters of phosphoric acid, acetic acid (for example ethyl acetate) and its homologues, particularly trimethylacetic acid, propionic acid, butyric acid and valeric acid, esters of dicarboxylic acids, and in addition aliphatic ethers. Especially suited solvents for the method of the invention are ethyl acetate, ethyl propionate, ethyl butyrate, methyl acetate, methyl propionate, methyl butyrate, trioctyl phosphate, dimethyl ether, diethyl ether, diisopropyl ether.

For reaction purposes, the acid calcium epoxysuccinate is suspended in the organic solvent, an equimolar amount of sulphuric acid is added, and the suspension is stirred for from 1 to 8 hours at temperatures of from 20° to 80° C. The liberated organic acids are thereby dissolved, while the insoluble calcium sulphate remains in suspension. On completion of the reaction the calcium sulphate is separated, for example by filtration, and the freed organic acids are removed by liquid-liquid extraction with water or an aqueous medium from the organic solvent which is used for further reactions. The epoxysuccinic acid in the aqueous phase is converted into tartaric acid by boiling for several hours and, after cooling, the tartaric acid is separated by crystallisation, while the mother liquor still containing tartaric acid is recycled to the aqueous phase between extraction and hydrolysis.

The freed organic acids can be recovered in other ways, which are known per se, apart from liquid-liquid extraction, for example by evaporation, crystallisation, precipitation or the like. In this case the organic solvents in which epoxysuccinic acid is soluble may comprise, apart from the compounds already mentioned, aliphatic alcohols, aliphatic ketones, aliphatic monocarboxylic acids, or cyclic ethers.

b. The organic solvent is miscible with water. These solvents may be the aliphatic alcohols, aliphatic and other water-miscible ketones, monocarboxylic acids, particularly aliphatic monocarboxylic acids, and cyclic ethers (for example dioxane). It is in such cases not necessary to use anhydrous solvent. In many cases it is even advantageous to use a mixture of organic solvent and water, because in this way the sensitivity of the organic solvent to sulphuric acid can be greatly reduced. The reaction is effected by introducing the acid calcium epoxysuccinate into the solvent and adding an equimolar amount of sulphuric acid.

The suspension is stirred for from 1 to 8 hours at from 20° to 80° C. and thereupon the calcium sulphate is filtered off.

The freed organic acids in dissolved form can than be recovered in two ways. If the preceding reaction was carried out in an anhydrous organic solvent of the kind indicated, this solvent can be concentrated or cooled, after separation of the calcium sulphate, to a point below the solubility product for epoxysuccinic acid, and the latter can be crystallised out on cooling. This procedure may in principle also be applied to the water-immiscible solvents mentioned for liquid-liquid extraction. The epoxysuccinic acid is then separated, dissolved in water, and hydrolysed in conventional manner. The filtrate saturated with epoxysuccinic acid can be added to the next charge, after filtering off the calcium sulphate.

When working with a mixture of water and organic, water-miscible solvent, it is preferable to use a solvent having a lower boiling point than water. On completion of the reaction and after separation of the calcium sulphate, the solvent can simply be distilled off, leaving behind an aqueous solution of epoxysuccinic acid. This solution can be fed direct to the hydrolysis stage. In the case where a mixture of water and solvent is used, a mixture of water with an alcohol or water with an aliphatic ketone in the ratio of 1:10 to 10:2 is preferred.

SPECIFIC EXAMPLES OF THE INVENTION

The invention will now be further illustrated with the aid of the following non-limiting Examples.

EXAMPLE 1

For the epoxidation of maleate to succinate the procedure was as follows:

The reactor used was a two-liter glass flask equipped with a stirrer, thermometer, and reflux condenser. Heating was effected by means of a thermostatically controlled bath. The starting solution originally contained:

| | |
|---|---|
| Acid calcium maleate | 67.6 g. |
| Tungstic acid | 0.8 g. |
| Water | 400.0 g. |
| Hydrogen peroxide, 70 per cent by weight | 24.3 g. |

The epoxidation was effected at a bath temperature of 60° C.. After about 10 minutes the internal temperature rose by about 2° to 3° C. in consequence of the exothermal reaction. At the same time, acid calcium epoxysuccinate began to crystallise out of the clear solution. The hydrogen peroxide content of the reaction solution was monitored analytically. Within from 60 to 80 minutes it fell to zero. At intervals of 1 hour, equimolar amounts of acid calcium maleate (67.6 g.) and hydrogen peroxide (24.3 g., 70% by weight) were added. This procedure was repeated eight times. After a total reaction time of 8 hours the reaction solution had a total weight of 1136 g. and the suspension was still just effectively stirrable. For the purpose of separating the acid calcium epoxysuccinate, a filtration stage then followed. For this purpose the reaction solution was cooled to cooling water temperature, and the acid calcium epoxysuccinate was filtered off and washed with 100 ml. of water. The reaction solution and washing water were immediately recycled to the epoxidation reactor.

From two moles of acid calcium maleate 644 g. of acid calcium epoxysuccinate containing 10% of water, corresponding to 580 g. of dry salt, were obtained. Since the theoretical yield amounts to 604 g., a yield of 96% of the theoretical, referred to hydrogen peroxide was obtained. Since the missing 4% of acid calcium maleate is contained in the mother liquor, the yield losses can be attributed only to the decomposition of the hydrogen peroxide.

The excess of acid calcium maleate is left in the mother liquor until it has attained 0.25 mole (67.6 g.), and then only hydrogen peroxide, without calcium maleate, is added once. If dry calcium maleate is used for the epoxidation, the water economy remains largely constant. If damp calcium salt is introduced into the system, the excess water can be distilled off by applying a vacuum at the end of the epoxidation reaction.

The reaction with sulphuric acid in an organic medium, followed by hydrolysis, was carried out as follows.

The acid calcium epoxysuccinate obtained by the epoxidation was reacted in acetic acid and the aid of concentrated sulphuric acid to form calcium sulphate and epoxysuccinic acid. For this purpose, 50 g. of acid calcium epoxysuccinate, having a calcium content of 11.9% by weight, and 15 g. of concentrated sulphuric acid were introduced, with stirring, into 300 ml. of glacial acetic acid. The suspension was kept at 20° C. for 2 hours with stirring, and then heated to 70° C. After 2 more hours the reaction was complete and the calcium sulphate was filtered off. The calcium sulphate was washed three times with 30 ml. of glacial acetic acid.

The filtrate and the acetic acid used for washing from two reactions carried out in this manner were united and the amount of acetic acid (390 ml.) corresponding to a reaction were distilled off. The distillation residue consisting of epoxysuccinic acid dissolved in acetic acid was then cooled, and the epoxysuccinic acid was crystallised out with stirring. The epoxysuccinic acid was then filtered off, dried, thereafter dissolved in water, and hydrolysed to tartaric acid in this solution.

In the procedure described above, about 38 g. dry epoxysuccinic acid were isolated per charge. From two moles of acid calcium epoxysuccinate it was possible to obtain 592 g. of epoxysuccinic acid, corresponding to a yield of 95% of the theoretical. Since the damp calcium epoxysuccinic introduced a certain amount of water into the system, it was necessary for the acetic acid distilled off to be freed of water in order to enable it to be used again.

EXAMPLE 2

The epoxidation of acid calcium maleate was effected in accordance with Example 1. 50 g. of the calcium epoxysuccinate attained in this manner (calcium content 11.9% by weight) were suspended, with stirring, in 400 g. of 50% aqueous acetone. 15 g. of concentrated sulphuric acid were then added and the suspension was kept for 2 hours at 20° C. If the suspension is made in acetone alone, a corresponding amount of dilute sulphuric acid may be added instead of concentrated sulphuric acid. The suspension was then heated to 50° C. and, after being kept for 2 hours at this temperature, the calcium sulphate was filtered off and washed with water. The acetone was removed by distillation from the mixture of acetone and water, and the remaining aqueous epoxysuccinic acid solution was subjected directly to hydrolysis. From two moles of acid calcium epoxysuccinate, 512 g. of free epoxysuccinic acid were obtained, corresponding to a yield of 97% of the theoretical.

EXAMPLE 3

An acid calcium epoxysuccinate (50 g., calcium content 11.9% by weight) produced by the procedure of Example 1 were introduced, with stirring, into 400 g. of trioctyl phosphate. 15 g. of concentrated sulphuric acid were then added and the suspension was kept at 20° C. for 2 hours whereupon it was heated to 70° C.. After 30 minutes at 70° C., the reaction was complete and the calcium sulphate was separated from the solvent by filtration. The epoxysuccinic acid was removed from the trioctyl phosphate by liquid-liquid extraction with water.

In a laboratory test, the trioctyl phosphate was shaken up three times with 100 ml. of water each time, whereupon after a few repetitions equilibrium was achieved and on each occasion the entire amount of epoxysuccinic acid liberated by reaction could be brought into the aqueous phase. This phase was in addition freed from the remaining trioctyl phosphate in a separator, and thereupon the epoxysuccinic acid was hydrolysed to tartaric acid direct in the aqueous solution by boiling for several hours.

The yield in the reaction effected in trioctyl phosphate amounted to 96%. From 2 moles of acid calcium epoxysuccinate, 507 g. of free epoxysuccinic acid in aqueous solution were obtained.

In order to avoid losses of solvent, the calcium sulphate was subjected to washing with acetone. For this purpose the calcium sulphate was washed on a filter with four times the amount of acetone. From the mixture of acetone and trioctyl phosphate the acetone was distilled off and the remaining trioctyl phosphate was returned to the solvent circuit.

EXAMPLE 4

For the epoxidation a 2-liter glass flask provided with an agitator, thermometer, and reflux condenser was used, and heating was effected by means of a thermostatically controlled bath. The starting solution had the following composition:

| | |
|---|---|
| Acid calcium maleate | 540.4 g. (2 moles) |
| Tungstic acid | 1.0 g. |
| Water | 500.0 g. |
| Hydrogen peroxide, 70% by weight | 23.3 g. (0.5 mole) |

The epoxidation was effected at 60° C. Of the 540 g. of acid calcium maleate used, about 165 g. were dissolved at 60° C., while the rest remained suspended in the solution and dissolved as the reaction progressed. 0.5 mole of hydrogen peroxide was added per hour, and the dissolved acid calcium maleate was thereby epoxidised to acid calcium epoxysuccinate, which crystallised immediately. 0.5 mole of hydrogen peroxide was added on eight occasions, and after a reaction time of 8 hours the acid calcium epoxysuccinate was filtered off. The yield referred to hydrogen peroxide was 1 to 2% lower in comparison with Example 1, and thus amounted to about 94 to 95% of the theoretical. When working with charges of two moles, it was possible to isolate about 568 g. of dry calcium epoxysuccinate. As regards water economy and the treatment of the excess calcium maleate, the same remarks as were made in respect of Example 1 are applicable.

The reaction with sulphuric acid of the acid calcium epoxysuccinate obtained in the manner described and the hydrolysis of the liberated epoxysuccinic acid were then carried in the manner described in Examples 1 to 3, similar results being obtained.

We claim:

1. In a method of producing tartaric acid comprising the steps of epoxidising acid calcium maleate in a reaction medium with hydrogen peroxide in the presence of a tungstic acid-containing catalyst, reacting the resulting acid calcium epoxysuccinate with sulphuric acid to form calcium sulphate and epoxysuccinic acid, and effecting hydrolysis of said epoxysuccinic acid to tartaric acid in an equeous medium, the improvement comprising separating the acid calcium epoxysuccinate from the reaction medium, transferring said acid calcium epoxysuccinate into a solvent medium selected from the group consisting of organic solvents and mixtures of organic solvents and water, reacting the acid calcium epoxysuccinate in the solvent medium with sulphuric acid, separating calcium sulphate from the solvent medium, and recovering from said solvent medium liberated organic acids consisting essentially of epoxysuccinic acid in a substantially pure state and substantially free from calcium salt.

2. The method of claim 1, wherein the said acid calcium epoxysuccinate is transferred into an organic solvent which is substantially immiscible with water and in which epoxysuccinic acid is soluble, and wherein, after the reaction with sulphuric acid and separation of the calcium sulphate, the liberated organic acids in the solvent are recovered by liquid-liquid extraction into an aqueous medium in which the hydrolysis is effected.

3. The method of claim 2, wherein the aqueous medium is water.

4. The method of claim 2, wherein the organic solvent is selected from the group consisting of esters of phosphoric acid, esters of aliphatic monocarboxylic acids, esters of dicarboxylic acids and aliphatic ethers.

5. The method of claim 1, wherein the acid calcium epoxysuccinate is transferred into an organic solvent in which epoxysuccinic acid is soluble, and wherein, after the reaction with sulphuric acid and separation of the calcium sulphate, the liberated organic acids consisting essentially of epoxysuccinic acid are crystallised out, separated, dissolved in water and hydrolysed to tartaric acid.

6. The method of claim 5, wherein the reaction with sulphuric acid is effected with heating and the crystallisation is effected by cooling the reaction medium.

7. The method of claim 5, wherein, after the reaction with sulphuric acid and separation of the calcium sulphate, some of the organic solvent is distilled off.

8. The method of claim 6, wherein, after the reaction with sulphuric acid and separation of the calcium sulphate, some of the organic solvent is distilled off.

9. The method of claim 5, wherein the organic solvent is selected from the group consisting of esters of phosphoric acid, esters of aliphatic monocarboxylic acids, esters of dicarboxylic acids, aliphatic ethers, aliphatic alcohols, aliphatic ketones, aliphatic monocarboxylic acids and cyclic ethers.

10. The method of claim 1, wherein the solvent medium is a mixture of water and an organic solvent which is miscible with water and in which epoxysuccinic acid is soluble, and wherein after the reaction with sulphuric acid and separation of the calcium sulphate, the organic solvent is distilled off to leave the epoxysuccinic acid in the remaining aqueous medium in which the hydrolysis is effected.

11. The method of claim 10, wherein the organic solvent has a lower boiling point than water.

12. The method of claim 10, wherein the organic solvent is selected from the group consisting of aliphatic alcohols, aliphatic ketones, aliphatic monocarboxylic acids and cyclic ethers.

* * * * *